United States Patent
Igaki et al.

Patent Number: 5,733,327
Date of Patent: Mar. 31, 1998

[54] STENT FOR LIBERATING DRUG

[76] Inventors: Keiji Igaki, 1-21, Wakakusa 2-chome, Kusatsu-shi, Shiga 525; Hideo Tamai, 50-19, Miyake-cho, Moriyama-shi, Shiga 524, both of Japan

[21] Appl. No.: 663,173
[22] PCT Filed: Oct. 17, 1995
[86] PCT No.: PCT/JP95/02129
§ 371 Date: Jun. 14, 1996
§ 102(e) Date: Jun. 14, 1996
[87] PCT Pub. No.: WO96/11720
PCT Pub. Date: Apr. 25, 1996

[30] Foreign Application Priority Data

Oct. 17, 1994 [JP] Japan ................. 6-250859

[51] Int. Cl.⁶ .................................. A61F 2/06
[52] U.S. Cl. ........................................ 623/1
[58] Field of Search .................... 623/1, 11, 12; 606/194, 198

[56] References Cited

U.S. PATENT DOCUMENTS

| | | | |
|---|---|---|---|
| 4,548,764 | 10/1985 | Munteanu et al. | 261/75 |
| 5,019,096 | 5/1991 | Fox, Jr. et al. | 623/11 |
| 5,044,116 | 9/1991 | Gago et al. | 427/4 |
| 5,366,504 | 11/1994 | Andersen et al. | 623/1 |
| 5,423,885 | 6/1995 | Williams | 623/1 |
| 5,464,450 | 11/1995 | Buscemi et al. | 623/1 |
| 5,545,208 | 8/1996 | Wolff et al. | 623/12 |

FOREIGN PATENT DOCUMENTS

| | | |
|---|---|---|
| 0554082 A1 | 8/1993 | European Pat. Off. . |
| 0566245 A1 | 10/1993 | European Pat. Off. . |
| 0604022 A1 | 6/1994 | European Pat. Off. . |
| 6-221 | 1/1994 | Japan . |
| 6-7455 | 1/1994 | Japan . |
| 6-218063 | 8/1994 | Japan . |

*Primary Examiner*—Michael J. Milano
*Assistant Examiner*—Tram Anh T. Nguyen
*Attorney, Agent, or Firm*—Limbach & Limbach LLP

[57] ABSTRACT

A stent according to the present invention is adapted to be introduced into a vascular system such as blood vessels. The stent includes a stent body produced by weaving or knitting a fiber containing a drug and made of a low-melting biodegradable polymer into a tubular shape, or coating a drug-containing low-melting biodegradable polymer on a stent body. When the stent is introduced into the vascular system, the drug contained therein is dosed in a locally limited region of the vascular system. The low-melting biodegradable polymer used has a melting point of 80° C. or lower and is at least one compound selected from the group consisting of poly-ε-caprolactone, poly-D, L-deca-lactone, polydioxane and a copolymer thereof.

3 Claims, 4 Drawing Sheets

STENT FOR LIBERATING DRUG

TECHNICAL FIELD

This invention relates to a stent for liberating a drug which is introduced into a vascular system such as blood vessels, and more particularly to a stent used for a local dosage of the drug.

BACKGROUND ART

For instance, in angioplasties, vascular walls are likely to be damaged by insertion of a catheter such as a balloon catheter or an atheroma-resecting catheter thereinto so that there occurs proliferation of the tunica intima due to a healing reaction in the vascular walls, which frequently results in a so-called restenosis.

Such restenosis is caused by a hyperplasia of smooth muscle cells and a majority of the recurrence of the disease is ascertained by an angiography, for example, 3 months after the angioplasty operation.

The frequency of the restenosis sums to about 30 to 40% though it varies depending upon facilities used in the angioplasty operation. If any restenosis does not occur 3 months after the operation, it is suggested that the restenosis is no longer caused subsequently.

Meanwhile, any method for preventing the aforementioned restenosis has not yet been established. However, attempts, which have been made for this purpose until now, include methods in which an instrument such as a stent or an atheroma-resecting catheter is used, or other methods to which genetic engineering is applied or in which drugs such as an antimetabolite, e.g., a carcinostatic agent, a fibroblast hyperplasia-preventing agent, or the like are used.

However, in the event that the catheter, for example, the atheroma-resecting catheter, is used to prevent the restenosis of blood vessels, patients suffer from significant pain and such an operation can be repeated only in a limited manner.

In addition, introduction of the stent into a portion subjected to the angioplasty provides some effect to prevent obliteration of blood vessels. However, since the stent itself has no function for restricting hyperplasia of smooth muscle cells and preventing the restenosis, the essential problem still remains unsolved. Moreover, upon the introduction of the stent into a portion subjected to the angioplasty, there is a possibility that thrombus will occur. Under these circumstances, in the event that the stent is used, in order to prevent occurrence of such thrombus, there has been proposed a method in which dosage of an antithrombotic agent such as dextran, aspirin, warfarin, or the like is used.

On the other hand, it is considered that dosage of drugs capable of restricting hyperplasia of smooth muscle cells is effective to prevent restenosis without use of instruments such as the stent, because such dosed drugs can function so as to prevent restenosis itself. However, in this case, some problems have been posed with respect to the dosage method of these drugs.

Similarly, in the event that the stent is used together with the antithrombotic agent to prevent thrombus, some problems have been also posed on the dosage of the antithrombotic agent.

In consequence, a locally limited dosage is regarded as an effective method for dosage of the drugs capable of restricting hyperplasia of smooth muscle cells or the antithrombotic agent. The locally limited dosage is carried out by a method in which a so-called dispatch catheter is used, a method in which a sweat balloon catheter is used, a method in which a double balloon catheter is used, a method in which the drugs are selectively introduced through a catheter, or the like.

The dispatch catheter is composed of a non-porous polyurethane sheath and a spiral coil wound around the polyurethane sheath. Drugs to be dosed are supplied into the spiral coil so that the drugs can be brought into contact with walls of blood vessels. The sweat balloon catheter contains a balloon having a microporous structure. When such a sweat balloon catheter is used, drugs are gradually dosed through fine pores of the balloon into an interior of the blood vessels. The double balloon catheter contains two balloons by which opposite ends of the portion subjected to the angioplasty are closed such that drugs are introduced through the catheter into a portion of the blood vessel between these balloons.

The aforementioned locally limited dosage methods can advantageously increase the concentration of the drug to be dosed, because the dosage of the drug is carried out in the locally limited region. To the contrary, since it is necessary to continuously retain the catheter in the blood vessel and thereby block a bloodstream, the locally limited dosage has such a disadvantage that it cannot be used over a long period of time. For instance, in the event that the sweat balloon catheter or the double balloon catheter is used, the locally limited dosage must be carried out within several minutes. Whereas, even in the event that the dispatch catheter is used or the drug is selectively introduced through the catheter, the time required for the dosage of the drug is limited to several hours. In addition, these methods have a further problem in that they can be carried out only in an operating room.

Moreover, it is known that a whole-body dosage is made by a peroral, transcutaneous or transluminal dosage of drugs so that the drugs are circulated through the whole body and reaches aimed cells. The whole-body dosage has an advantage in that it can be used over a long period of time.

However, in case of the whole-body dosage, the concentration of the drug in the blood is undesirably raised so that there is a possibility that unexpected side effects such as hepatopathy, an aspiration accident, an excess or failed dosage will occur. In addition, when an antithrombotic agent is dosed by the whole-body dosage method, fine arteries and veins in a brain are damaged so that an intracerebral hemorrhage is likely to occur. Moreover, in case where a long-term dosage is made, a large amount of drug is dosed such that a huge medical expense is required.

As described above, although many attempts have been made to prevent restenosis, for example, after an angioplasty operation, any effective method which makes the locally limited and long-term dosage of drugs possible, has not yet been found until now.

DISCLOSURE OF THE INVENTION

The present invention has been accomplished to overcome the aforementioned problems. It is therefore an object of the present invention to provide a novel stent for liberating or eluting a drug, which is capable of a locally limited and long-term dosage of the drug.

As a result of long-term intense investigations and studies made by the present inventors, the stent has been developed based on a novel concept.

That is, in accordance with the present invention, there is provided a stent which is adapted to be introduced into a vascular system such as blood vessels. The stent is composed of a stent body formed by weaving or knitting a fiber, which contains a drug and is made of a biodegradable polymer having a low-melting point at which pharmacological effects of the drug are not damaged, into a tubular body.

In this case, the amount of the drug to be added to the biodegradable polymer is determined depending upon the kind of drug thereof. When the amount of the drug in the biodegradable polymer is too small, the drug released into the vascular system decreases so that an effect by the dosage of the drugs cannot be exhibited to a sufficient extent. On the other hand, when the amount of the drugs in the biodegradable polymer is too large, the healing process in walls of blood vessels is completely restricted so that formation of fibers or coats becomes difficult.

The kind of drug added may be selected according to the symptom or the aimed use. Examples of such drugs may include an antimetabolite such as a carcinostatic, a fibroblast hyperplasia-preventing agent, an antithrombotic agent or the like.

The drugs as a solute are dissolved in the biodegradable polymer as a solvent to form a solution. The solution is then hardened into a fiber from which the stent is prepared. Alternatively, the solution may be coated on a rigid stent body having an adequate mechanical strength, for example, a metal stent body or a tubular woven or knitted stent body made of a biodegradable polymer having a high melting point.

In this case, when heated to an elevated temperature, the drug is susceptible to undesired change in its molecular structure, which leads to loss of the aimed effect or conversion to a toxic substance.

In general, the biodegradable polymer used as sutures, for example, poly-lactic acid or poly-glycolic acid, has a melting point ranging from about 220° C. to about 240° C. Consequently, there might occur an inconvenience that the drugs added thereto is subjected to undesired chemical conversion, when heated to such elevated temperature.

Accordingly, it is required that the biodegradable polymer have a low meting point at which the drug added can be present without loss of the pharmacological effects. For example, it is desirable to have the melting point of the biodegradable polymer at 80° C. or lower.

Examples of suitable low-melting biodegradable polymers may include poly-ε-caprolactone, poly-D, L-decalactone, poly-di-oxanone or a copolymer of these compounds, which have a melting point of about 63° C.

However, the aforementioned low-melting biodegradable polymers cannot necessarily exhibit sufficient mechanical strength. In consequence, it is suitable that the fiber composed of the low melting biodegradable polymer containing the drug be woven or knitted together with those made of a high-melting biodegradable polymer to form the tubular stent body.

On the other hand, the drug added may include an antimetabolite such as a carcinostatic, a fibroblast hyperplasia-preventing agent, or the like. For the purpose of preventing restenosis, TRANIRAST is the preferred drug.

TRANIRAST is an oral anti-allergic agent and widely used as remedies for bronchial asthma, allergic thiniris or atopic dermatitis. It has been recently found that TRANIRAST has an effect of restricting a hyperplasia of smooth muscle cells. As a result, the drug is expected to show a preventive effect against the restenosis. Actually, the present inventors have confirmed preventive effect of TRANIRAST against restenosis.

The stent according to the present invention is adapted to be introduced into a vascular system and retained in a particular region of the vascular system. At this time, the drug contained in the biodegradable polymer is released or eluted into the vascular system over 3 months in association with biodegradation of the stent. As a result, the drug contained in the biodegradable polymer is allowed to be continuously dosed into a locally limited region of the vascular system over a long period of time while maintaining its concentration in a constant level.

In this case, such a locally limited dosage of the drug can be carried out without any risk of causing adverse side effects as observed in the case of the whole-body dosage. In addition, this makes it possible to dose a relatively small amount of the drugs over a long period of time.

Moreover, differing from the conventional locally limited dosage, the present invention can provide a long-term dosage without inflicting serious pain on a patient.

BEST MODE FOR CARRYING OUT THE INVENTION

The present invention will be described in more detail by way of specific examples by referring to the accompanying drawings.

EXAMPLE 1

The present Example shows one example of a stent which is effective for preventing a restenosis after an angioplasty operation. In Example 1, a drug used there is TRANIRAST (N-(3, 4-dimethoxy-cinnamoyl)-anthranilic acid) represented by the following chemical formula:

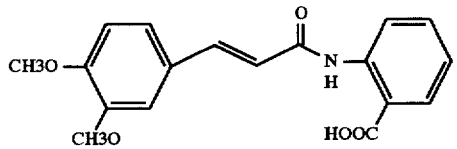

TRANIRAST is one of the fibroblast hyperplasia-preventing agents. Tamai et at., one of the inventors of the present application, reported that clinical experiments in which TRANIRAST was continuously dosed for 3 months at a dosage amount of 600 mg per day (one tablet after every meal), surprisingly showed a restenosis rate of 15% or lower. Consequently, the drug has been expected to provide a remarkable preventive effect against restenosis.

TRANIRAST was added to and dissolved in a biodegradable polymer composed of poly-ϵ-caprolactone having a melting point of about 63° C. to prepare a polymer solution.

The thus-prepared polymer solution was a mixture containing TRANIRAST in an amount of 1 to 2% by weight based on poly-ϵ-caprolactone.

The polymer solution was then subjected to a spinning process to prepare a fiber composed of a TRANIRAST-containing poly-ϵ-caprolactone.

Figure 1:
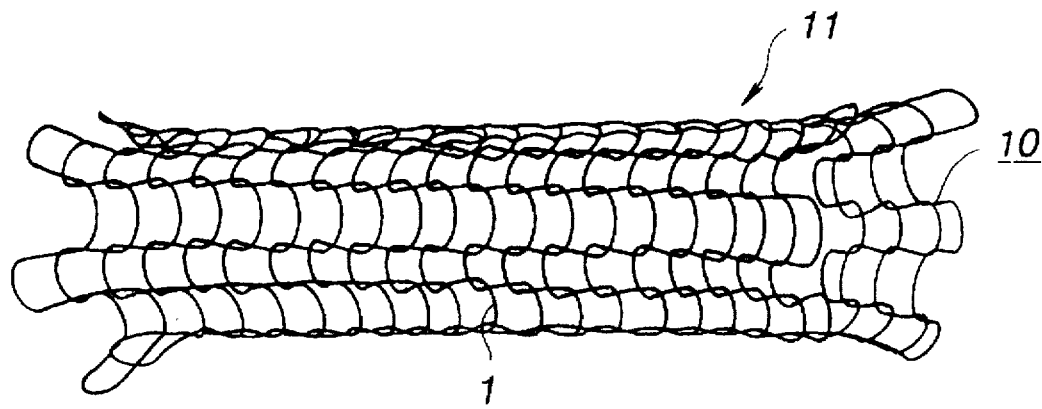
FIG. 1 is a perspective view schematically showing one embodiment of a stent according to the present invention.

Next, as shown in FIG. 1, the fiber composed of a TRANIRAST-containing poly-ϵ-caprolactone was knitted into a tubular shape to form a stent body 10. End portions of the fiber constituting the stent body were treated to obtain a stent 11.

The thus-obtained stent 11 was produced by knitting the poly-ϵ-caprolactone fiber 1 having a diameter of about 0.05 mm and a length of 90 cm into a tubular shape having a diameter of 3 mm and a length of 20 mm.

EXAMPLE 2

The present Example shows another example of a stent which is produced by knitting a drug-containing low-melting biodegradable polymer fiber and a high-melting biodegradable polymer fiber together.

In Example 2, as the drug-containing biodegradable polymer fiber, there was used the TRANIRAST-containing poly-ϵ-caprolactone fiber 1 prepared in the same manner as described in Example 1 above. The fiber was prepared in a similar manner to that of Example 1 by subjecting the polymer solution containing 1 to 2% by weight of TRANIRAST based on poly-ϵ-caprolactone to a spinning process.

Figure 2:
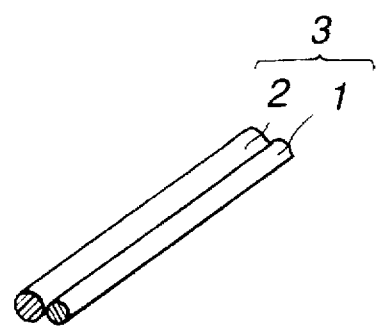
FIG. 2 is a perspective view schematically showing essential parts of two folded yarn composed of a fiber made of a high-melting biodegradable polymer and a fiber containing a drug and made of a low-melting biodegradable polymer.

The TRANIRAST-containing poly-ϵ-caprolactone fiber 1 and the high-melting biodegradable polymer fiber 2 was formed into a two folded yarn 3 as shown in FIG. 2. The two folded yarn 3 was knitted into a stent body 10 to obtain a stent 11.

In this case, the high-melting biodegradable polymer fiber 2 constituting the two folded yarn 3 was produced by subjecting poly-lactic acid or poly-glycolic acid to a spinning process.

In addition, the TRANIRAST-containing poly-ϵ-caprolactone fiber 1 constituting the two folded yarn 3 was a spun yarn having a diameter of about 0.05 mm. The high-melting biodegradable polymer fiber 2 was also a spun yarn having a diameter of about 0.05 mm. The stent body 10 was produced by knitting the two folded yarn having a length of 90 cm to a tubular body having a diameter of 3 mm and a length of 20 mm.

The size of the stent body 10 may be varied properly depending upon the vascular system to which the stent was applied.

Alternatively, the stent 11 can be formed by first knitting the stent body 10 and then coating the low-melting biodegradable polymer solution composed of a mixture of a solvent and a drug on the stent body 10, so that the amount of the drug contained in the stent can be controlled properly. In this case, as the low-melting biodegradable polymer solution, there is suitably used a mixture solution prepared by mixing 70 cc of acetone, 1 g of TRANIRAST and 1 g of poly-ϵ-caprolactone together. In the event that the solution is coated, it is desirable that the stent body 10 is subjected to a heat treatment to evaporate acetone as the solvent component.

In the foregoing, the two folded yarn 3 composed of the TRANIRAST-containing poly-ϵ-caprolactone fiber 1 and the high-melting biodegradable polymer fiber 2 was used to obtain the knitted stent body 10. However, a composite twisted yarn composed of plural TRANIRAST-containing poly-ϵ-caprolactone fibers 1 and plural the high-melting biodegradable polymer fibers 2 may be used for the purpose.

EXAMPLE 3

Figure 3:
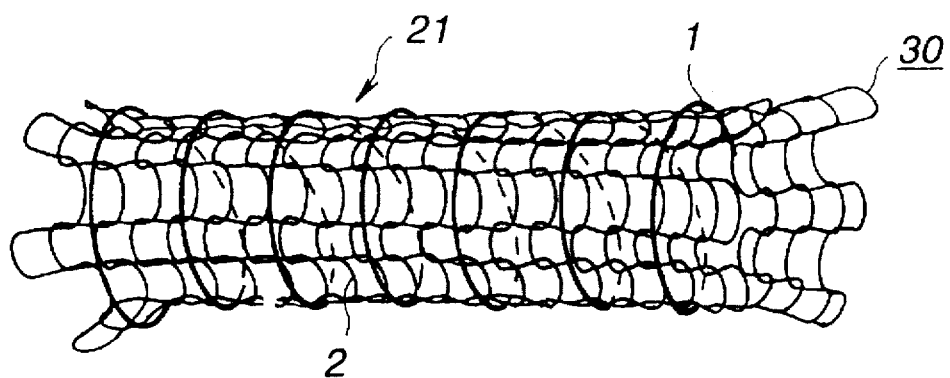
FIG. 3 is a perspective view schematically showing another embodiment of a stent according to the present invention.

In this Example, a high-melting biodegradable polymer fiber 2 was preliminarily knitted into a tubular shape to prepare a stent body 30. The TRANIRAST-containing poly-ϵ-caprolactone fiber 1 as the drug-containing low-melting biodegradable polymer fiber was wound around the stent body 30 in an interlocking relation to each other so as to form a stent 21, as shown in FIG. 3. The fiber 1 was also produced by subjecting the polymer solution containing 1 to 2% by weight of TRANIRAST based on poly-ϵ-caprolactone to a spinning process.

In addition, the high-melting biodegradable polymer fiber 2 used in this Example was also a poly-lactic acid fiber, a polyglycolic acid polymer fiber or a fiber composed of a copolymer thereof.

In this Example, the stent body 30 may be also coated with a polymer solution prepared by mixing 1 g of TRANIRAST as a drug and 1 g of poly-ϵ-caprolactone with 70 cc of acetone, so that the amount of TRANIRAST to be contained in the stent 20 can be controlled properly.

EXAMPLE 4

Figure 4:
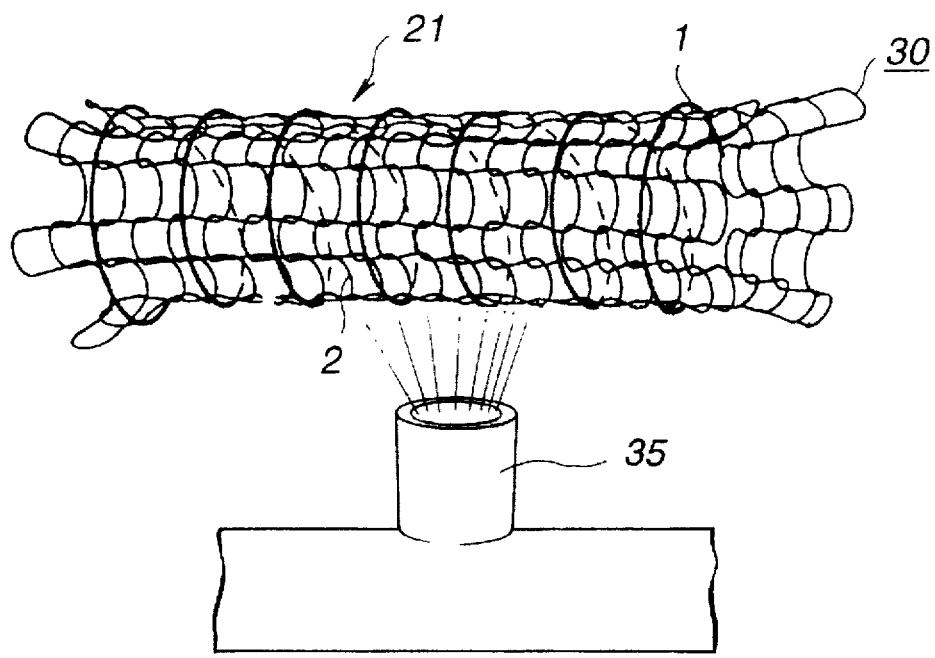
FIG. 4 is a perspective view showing the condition in which the fiber containing the drug and made of a low-melting biodegradable polymer is placed around a stunt body formed from a high-melting biodegradable polymer fibers and then melted so as to adhere to an outer surface thereof.

In this Example, using the same procedure as described in Example 3 above, the high-melting biodegradable polymer fiber 2 was preliminarily knitted into a tubular shape to form the stent body 30. The TRANIRAST-containing poly-ϵ-caprolactone fiber 1 as the drug-containing low-melting Biodegradable polymer fiber was then wound around an outer circumferential surface of the stent body 30 in an interlocking relation to each other so as to form a stent 21, as shown in FIG. 3. The thus-prepared stent 20 was heated by a heating means 35 as shown in FIG. 4 to smoothen an outer surface of the stent. The heating means 35 usable here may be a blower capable of blowing hot air.

Specifically, the stent 21 was heated to a temperature at which the TRANIRAST-containing poly-ϵ-caprolactone fiber 1 was not completely molten, namely up to the melting point of poly-ϵ-caprolactone or a temperature lower than the melting point, whereby an outer peripheral surface of the TRANIRAST-containing poly-ϵ-caprolactone fiber 1 was caused to melt so that the outer surface of the stent 21 was smoothened.

The TRANIRAST-containing poly-ϵ-caprolactone fiber 1 may be also produced by subjecting the polymer solution containing 1 to 2% by weight of TRANIRAST based on poly-ϵ-caprolactone to a spinning process. In addition of the high-melting biodegradable polymer fiber 2 may be also a poly-lactic acid fiber, a polyglycolic acid polymer fiber or a fiber composed of a copolymer thereof.

The smoothened outer surface of the stent 21 permits a smooth insertion of the stent into a vascular system such as blood vessels.

EXAMPLE 5

In this Example, a high-melting biodegradable polymer fiber 42 was coated with a solution of a drug-containing low-melting biodegradable polymer and then the coated fiber was knitted into a stent 41.

Figure 5:
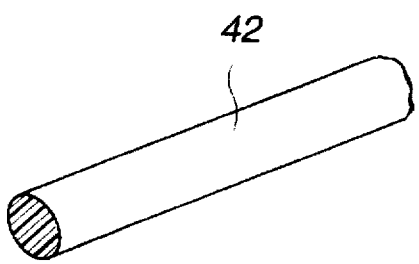
FIG. 5 is a perspective view showing a high-melting biodegradable polymer fiber which is knitted into a stent body of a stent according to a further embodiment of the present invention.

In the production of the stent 41, a biodegradable polymer material having a melting point higher than that of the drug-containing low-melting biodegradable polymer was subjected to a spinning process to obtain the biodegradable polymer fiber 42 as shown in FIG. 5. At this time, the high-melting biodegradable polymer fiber 42 used here may be fiber prepared by subjecting poly-lactic acid, polyglycolic acid or a copolymer thereof to a spinning process.

Figure 6:
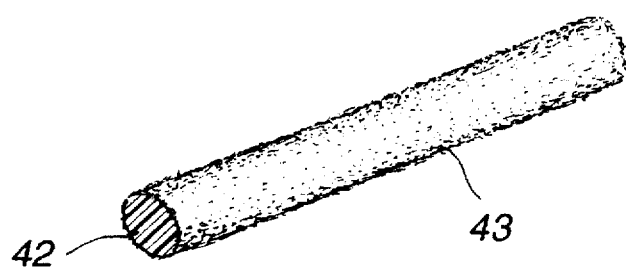
FIG. 6 is a perspective view showing the condition in which the fiber shown in FIG. 5 is coated with a solution composed of the low-melting biodegradable polymer containing the drug.

The biodegradable polymer fiber 42 was coated with a solution 43 of drug-containing low-melting biodegradable polymer as shown in FIG. 6. The solution 43 of drug-containing low-melting biodegradable polymer used here was a solution prepared by mixing 1 g of TRANIRAST as a drug and 1 g of poly-ϵ-caprolactone with 70 cc of acetone as a solvent.

Next, the high-melting biodegradable polymer fiber 42 on which the drug-containing low-melting biodegradable polymer solution 43 was coated, was knitted to form the stent 41.

Successively, the thus-knitted stent 40 was heated to evaporate acetone. The stent 40 was preferably heated to a temperature at which the drug-containing low-melting biodegradable polymer 43 was still maintained in an unmolten state. This was because melting of the drug-containing low-melting biodegradable polymer 43 was to be prevented upon heating.

Meanwhile, in the event that acetone as a solvent was already evaporated during production of the knitted stent body 40, the heating step can be omitted.

Figure 7:
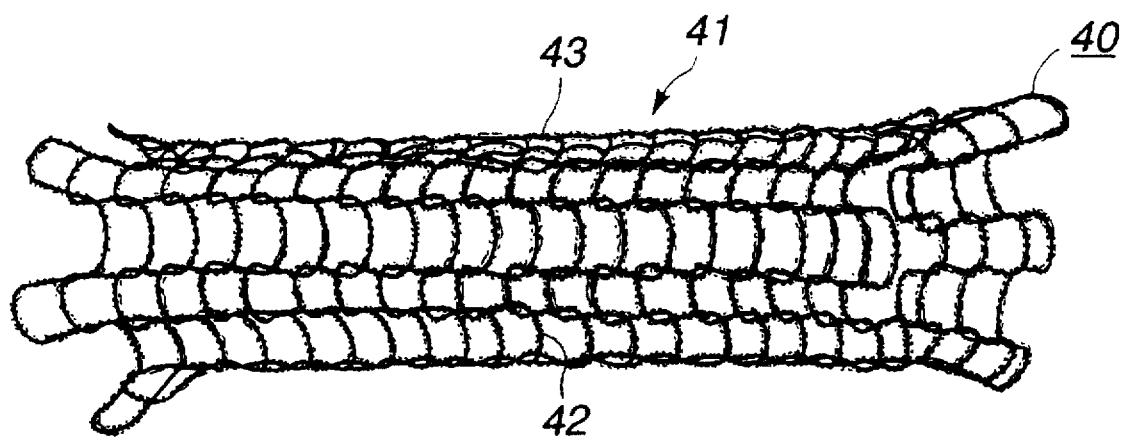
FIG. 7 is a perspective view showing a stent formed by knitting the high-melting biodegradable fiber which is coated with the solution composed of the low-melting biodegradable polymer containing the drug.

Thereafter, the stent body 40 from which acetone as a solvent was evaporated, was formed into the stent 41, as shown in FIG. 7, by treating end portions of the fiber 42 constituting the stent body 40.

In addition, the knitted stent body 40 may be further coated with the low-melting biodegradable polymer solution 43 prepared by mixing 1 g of TRANIRAST as a drug and 1 g of poly-ϵ-caprolactone with 70 cc of acetone so that the amount of TRANIRAST as a drug coated on the stent body 40, can be adjusted to a proper level. In this case, it is preferred that the stent body is heated to evaporate acetone as a solvent.

EXAMPLE 6

Figure 8:
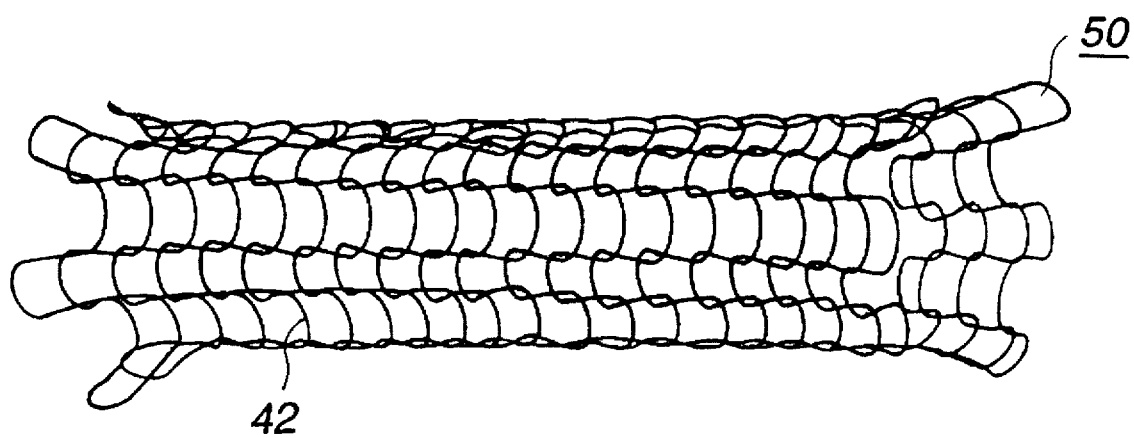
FIG. 8 is a perspective view showing a stent body formed from the fiber composed of the high-melting biodegradable polymer.
Figure 9:
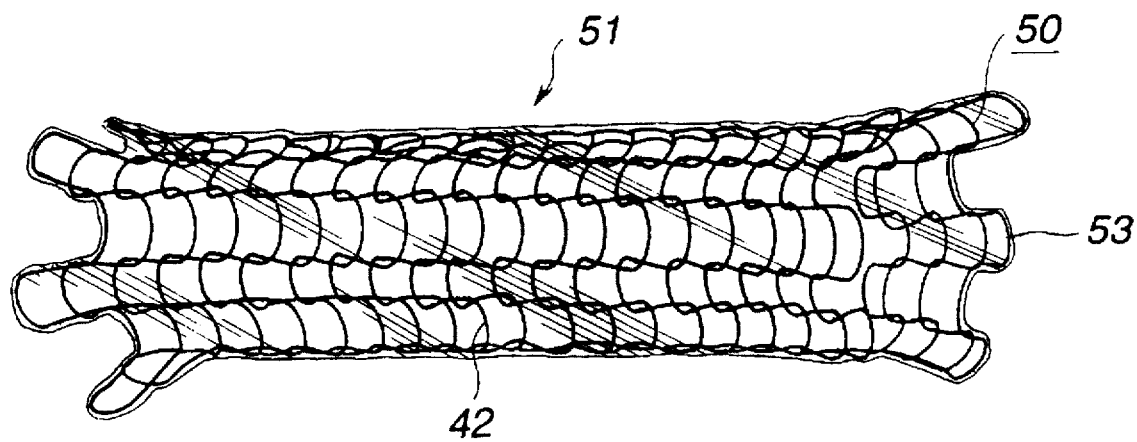
FIG. 9 is a perspective view showing a still further embodiment of a stent according to the present invention in which the stent body shown in FIG. 8 is coated with the drug-containing low-melting biodegradable polymer solution.

In the aforementioned Examples, the high-melting biodegradable polymer fiber was first coated with the solution of the drug-containing low-melting biodegradable polymer and then the fiber was knitted to form the stent. On the other hand, in this Example, the high-melting biodegradable polymer fiber 42 prepared by subjecting poly-lactic acid, polyglycolic acid or a copolymer thereof to a spinning process was first knitted into a stent boy 50 as shown in FIG. 8. Applied over the stent body 50 was a low-melting biodegradable polymer solution 53 containing a drug as shown in FIG. 9 to form a stent 51 of this Example.

The drug-containing low-melting biodegradable polymer solution 53 applied to the stent body 50 was a polymer solution containing 1 to 2% by weight of TRANIRAST based on poly-ϵ-caprolactone in the solution.

The application of the low-melting biodegradable polymer solution 53 to the stent body 50 may be carried out by coating the solution 53 over an outer circumferential surface thereof. Alternatively, the low-melting biodegradable polymer solution 53 may be applied to the stent body 50 by immersing the stent body 50 therein.

EXAMPLE 7

This Example shows a further example of a stent which is produced by coating a drug-containing biodegradable polymer solution over a stent body.

Figure 10:
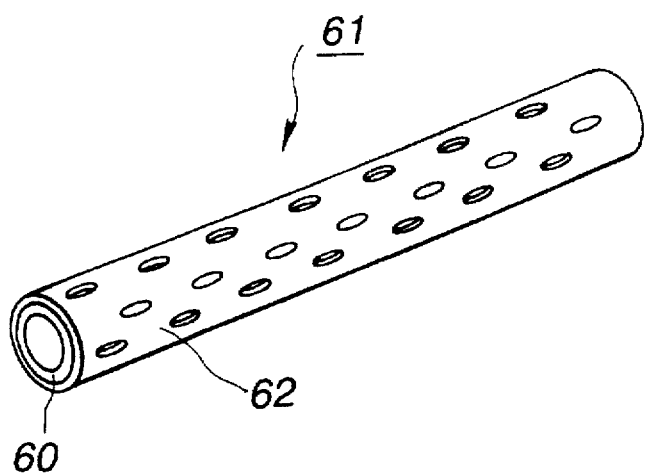
FIG. 10 is a perspective view showing a still further embodiment of a stent according to the present invention.

In this Example, a stent 61 was produced by coating the drug-containing biodegradable polymer solution on the stent body made of metal to form a layer 62 composed of drug-containing biodegradable polymer over an outer surface of the stent body 60, as shown in FIG. 10. The solution coated contained 1 to 2% by weight of the drug based on poly-ϵ-caprolactone (having a melting point of 63° C.) in the solution.

The stent body 60 used above was made of a metal material having a thickness of 0.05 mm to 0.1 mm and formed into a cylindrical body having a diameter of 2.5 mm to 4 mm and a length of 15 mm to 25 mm. Examples of the metal material may include stainless steel, tantalum or the like.

The stent prepared in each of the aforementioned Examples was introduced into the blood vessel after angioplasty operation and held in place. As a result, it was confirmed that dosage of TRANIRAST was carried out in an adequate manner for a long period of time, whereby occurrence of the restenosis was considerably reduced.

INDUSTRIAL APPLICABILITY

As is apparently understood from the aforementioned detailed description, the use of the stent according to the present invention enables a continuous, locally limited and long-term dosage of the drug.

In addition, such a dosage can prevent occurrence of side effects so that pains inflicted on patients can be minimized.

What is claimed is:

1. A stent for liberating TRANIRAST, which is adapted to be introduced into a vascular system such as blood vessels, comprising a stent body produced by weaving or knitting into a tubular shape a fiber containing TRANIRAST and made of a low-melting biodegradable polymer having a melting point at which no pharmacological effects of TRANIRAST are damaged.

2. A stent for eluting TRANIRAST contained therein, comprising a stent body coated with a mixture composed of TRANIRAST and a low-melting biodegradable polymer having a melting point at which no pharmacological effects of TRANIRAST are damaged.

3. A stent for liberating a drug, which is adapted to be introduced into a vascular system such as blood vessels, comprising:

a stent body produced by weaving or knitting into a tubular shape a composite fiber composed of fiber made of a low-melting biodegradable polymer having a melting point at which no pharmacological effects of the druq are damaged and a fiber made of a high-melting biodegradable polymer having a melting point higher than that of the fiber composed of the low-melting biodegradable polymer;

wherein the low-melting biodegradable polymer exposed to an outer surface of the stent body is heat-fused to smoothen the outer surface;

wherein the high-melting biodegradable polymer is at least compound selected from the group consisting of poly-lactic acid, polyglycolic acid and a copolymer thereof;

wherein the melting point of the low-melting point biodegradable polymer is 80° C. or lower; and wherein the composite fiber constituting the stent body is a two folded yarn, the two folded yarn including a TRANIRAST-containing poly-$\epsilon$-caprolactone fiber.

* * * * *